US008603522B2

(12) United States Patent
Bartels et al.

(10) Patent No.: US 8,603,522 B2
(45) Date of Patent: Dec. 10, 2013

(54) NUTRITIONAL SUPPLEMENT TO TREAT MACULAR DEGENERATION

(75) Inventors: Stephen Paul Bartels, Pittsford, NY (US); Cara Larraine Baustian, Palisades, NY (US); George Edwin Bunce, Blacksburg, VA (US); Leon Ellenbogen, New City, NY (US); Frederick L. Ferris, III, Columbia, MA (US); Jin Kinoshita, El Macero, CA (US); James Cecil Smith, Jr., Glenn Dale, MD (US); David A. Souerwine, Pittsford, NY (US)

(73) Assignee: Bausch & Lomb Incorporated, Rochester, NY (US)

(*) Notice: Subject to any disclaimer, the term of this patent is extended or adjusted under 35 U.S.C. 154(b) by 1775 days.

(21) Appl. No.: 11/034,656

(22) Filed: Jan. 13, 2005

(65) Prior Publication Data

US 2005/0163864 A1 Jul. 28, 2005

Related U.S. Application Data

(63) Continuation of application No. 10/641,668, filed on Aug. 15, 2003, now abandoned, which is a continuation of application No. 09/816,284, filed on Mar. 23, 2001, now Pat. No. 6,660,297.

(51) Int. Cl.
*A61K 9/20* (2006.01)

(52) U.S. Cl.
USPC .......... 424/464; 424/400; 424/427; 424/451; 424/489

(58) Field of Classification Search
None
See application file for complete search history.

(56) References Cited

U.S. PATENT DOCUMENTS

| | | | |
|---|---|---|---|
| 5,075,116 A | 12/1991 | LaHaye et al. | 424/617 |
| 5,607,707 A | 3/1997 | Ford et al. | 426/2 |
| 5,739,156 A | 4/1998 | Bissett | 514/458 |
| 5,770,217 A | 6/1998 | Kutilek, III et al. | 424/442 |
| 5,948,443 A | 9/1999 | Riley et al. | 424/643 |
| 5,976,568 A | 11/1999 | Riley | 424/451 |
| 6,020,351 A | 2/2000 | Pero | 514/355 |
| 6,103,756 A | 8/2000 | Gorsek | 514/458 |

FOREIGN PATENT DOCUMENTS

| | | |
|---|---|---|
| DE | 200 12 510 U1 | 11/2000 |
| EP | 0 930 072 | 7/1999 |
| GB | 2 301 775 A | 12/1996 |
| GB | 2301775 A | 12/2006 |
| WO | WO 01 19383 | 3/2001 |
| WO | WO 01 91765 | 12/2001 |

OTHER PUBLICATIONS

Control Clin Trials, 20(6) pp. 573-600 (1999).*
Inter Partes Reexam of US 6660297, Exhibit A, "Consents and Decrees re 03-CV-6619 T(P), 2004-2005,".
Inter Partes Reexam of US 6660297, Exhibit B, "Prevention's Healing Vitamins," Various pages, 1996, Rodale Press Inc.,.
Inter Partes Reexam of US 6660297, Exhibit C, Kulick, "Nutrition supplement usage recomendation by eye care specialists for macular degeneration of the eye: a statewide survey of Michigan," Top Clin Nutr, 1995, (vol. 10), (Issue. 4), (p. 67-77).
Inter Partes Reexam of US 6660297, Exhibit D, "Ocuvite Formulations, 1996-1997,".
Inter Partes Reexam of US 6660297, "Comments by Third Party Rexall," (Mar. 20, 2008).
Inter Partes Reexam of US 6660297, "The age-related eye disease study: a clinical trial of zinc and antioxidants—age-related eye disease study report No. 2," Amer Soc for Nutr Sci, 2000, (p. 1516S-19S).
Inter Partes Reexam of US 6660297, "Amendment under 37 CFR 1.530(D)," (Feb. 19, 2008).
Inter Partes Reexam of US 6660297, "Reexamination Communication," (Dec. 21, 2007).
Age-Related Eye Disease Study Research Group: "A Randomized Placebo-Controlled, Clinical Trial of High-Dose Supplementaion with Vitamins C and E, Beta Carotene and Zinc for Age-Related Macular Degeneration and Vision Loss: AREDS Report No. 8" Archives of Ophthalmolgy, vol. 119, No. 10, Oct. 2001, pp. 1417-1436.
Age-Related Eye Disease Study Research Group: "A Randomized Placebo-Controlled, Clinical Trial of High-Dose Supplementaion with Vitamins C and E and Beta Carotene for Age-Related Cataract and Vision Loss: AREDS Report No. 9" Archives of Ophthalmolgy, vol. 119, No. 10, Oct. 2001 pp. 1439-1452.
Age-Related Eye Disease Study Research Group, The Age-Related Eye Disease Study: A Clinical Trial of Zinc and Antioxidants—Age Related Eye Disease Study Report No. 2, Journal of Nutrition 2000.
R. E. Wyszynski, A Donor-Age-Dependent Change in the Activity of Alpha-Mannosidase in Human Cultured RPE Cells, Investigative Ophthalmology & Visual Science, vol. 30, No. 11, Nov. 1989, pp. 2341-2347.
D. B. Milne, Effect of Ascorbic Add on Copper and Cholesterol in Adult Cynomolgus Monkeys Fed a Diet Marginal in Copper, The American Journal of Clinical Nutrition, Nov. 1981, pp. 2389-2393.
D. B. Milne, Effects of Ascorbic Acid of Supplements and a Diet Marginal in Copper on Indices of Copper Nutriture in Women, Nutrition Research, vol. 8, 1988, pp. 865-873.
Copper Responsive Anemia, Induced by Oral Zinc Therapy in a Patient with Acrodermatitis Enteropathica Authors: Hoogenraad, et al. Sci Total Environ, Mar. 15, 1985:42 (1-2):37-43.

(Continued)

*Primary Examiner* — Hasan Ahmed
(74) *Attorney, Agent, or Firm* — Joseph Barrera; Toan P. Vo

(57) ABSTRACT

A daily nutritional or dietary supplement composition that strengthens and promotes retinal health through the prevention, stabilization, reversal and/or treatment of visual acuity loss by reducing the risk of developing late stage or advanced age-related macular degeneration in persons with early age-related macular degeneration. The ingredients of the daily nutritional or dietary supplement composition include vitamin C, vitamin E, lutein, zinc and copper. The ingredients are preferably provided in a tablet form suitable for oral ingestion.

20 Claims, No Drawings

(56) References Cited

OTHER PUBLICATIONS

Zinc-induced Copper Deficiency In an Infant Authors: Botash, et al. Am J. Dis Child, Jun. 1992, 146 (6):209-11.
Zinc-induced Copper Deficiency Authors: Hoffman, et al. Gastroenterology Feb. 1988, 94 (2):508-12.
Hypocupremia Induced by Zinc Therapy In Adults Authors: Prasad, et al. JAMA, Nov. 1978, 10, 240(20); 2166.8.
D. A. Newsome, Oral Zinc in Macular Degeneration, Arch. Ophthalmology—vol. 106, Feb. 1988, pp. 192-198 Storz Ophthalmics, A Closer Look at the Consequences of Radical Behavior in the Eye, Jul. 1997.
Sardi B: "Nutrition and the Eyes: Clearing up Misconception", Health Foods Business 1997, vol. 43, No. 8, pp. 29-30.
Olson R. J.: "Supplemental Dietary Antioxidant Vitamins and Minerals in Patients with Macular Degeneration", Journal of the American College of Nutrition, vol. 10, No. 5, 1991, p. 550.
Brown A. et al: "Nutrition Supplements and the Eye", EYE (London, England) England 1988, vol. 12 (Pt. 1, 1998, pp. 127 133.
Inter Partes Reexam of US 6660297, "US PTO Action Closing Prosecution," (Sep. 14, 2009).
Inter Partes Reexam of US 6660297, "Patent Owner's Response and Exhibits," (Nov. 13, 2009).
Inter Partes Reexam of US 6660297, "Patent Owner's Amendment to Claims," (Nov. 13, 2009).
Inter Partes Reexam of US 6660297, "Chew Affidavit," (Nov. 13, 2009).
Inter Partes Reexam of US 6660297, "Lugo Affidavit," (Nov. 13, 2009).
Inter Partes Reexam of US 6660297, "Polyn Affidavit," (Nov. 13, 2009).
Inter Partes Reexam of US 6660297, "Third Party Comments and Exhibits," (Dec. 14, 2009).
Israel, "Is AREDS changing practice patterns?," Ophthal Management, Jul. 2002.
Richer et al., "Double-masked, placebo-controlled, randomized trial of lutein and antioxidant supplementation in the intervention of atrophic age-related macular degeneration: the Veterans LAST study (Lutein Antioxidant Supplementation Trial)," Optometry, Apr. 2004, (vol. 75), (Issue. 4), (p. 216-229).
Chew et al., "Age-related eye disease study 2 protocol," Dec. 2007, (p. 1-20).
Clinical Studies Database, "Age-related eye disease study 2 (AREDS2)," National Eye Institute, p. 1-3.
AREDS Report No. 8, "A randomized, placebo-controlled, clinical trial of high-dose supplementation with vitamins C and E, beta carotene, and zinc for age-related macular degeneration and vision loss," Arch Ophthalmol, 2001, p. 1417-1436.
AREDS Report No. 9, "A randomized, placebo-controlled, clinical trial of high-dose supplementation with vitamins C and E and beta carotene for age-related cataract and vision loss ," Arch Ophthalmol., 2001, p. 1439-1452.
AREDS Report No. 11, "Potential public health impact of age-related eye disease study results," Arch Ophthal, Nov. 2003, p. 1621-1624.
Hall et al., "Prevention of age related macular degeneration," BMJ, p. 1-2, (Jul. 6, 2002).

* cited by examiner

NUTRITIONAL SUPPLEMENT TO TREAT MACULAR DEGENERATION

This application is a continuation of Ser. No. 10/641,668, filed Aug. 15, 2003, which is a continuation of Ser. No. 09/816,284, filed Mar. 23, 2001, now U.S. Pat. No. 6,660,297.

The U.S. Government has a paid-up license in this invention and the right in limited circumstances to require the patent owner to license others on reasonable terms as provided for by the terms of the Cooperative Research and Development Agreement (CRADA) awarded by the National Institutes of Health, Alcohol, Drug Abuse and Mental Health Administration.

FIELD OF THE INVENTION

The present invention relates to a nutritional or dietary supplement composition that strengthens and promotes retinal health through the prevention, stabilization, reversal and/or treatment of visual acuity loss in people with particular ocular diseases. More specifically, the present invention relates to an antioxidant and high-dosage zinc nutritional or dietary supplement composition that decreases visual acuity loss by reducing the risk of developing late stage or advanced age-related macular degeneration in persons with early age-related macular degeneration. The subject composition may likewise reduce the risk of vision loss associated with the development of cataracts.

BACKGROUND OF THE INVENTION

Macular degeneration associated with age and drusen is the leading cause of severe visual acuity loss in the United States and Western Europe in persons aged 55 years old or older. Age-related macular degeneration (AMD) is a collection of clinically recognizable ocular findings that can lead to blindness. The findings include drusen, retinal pigment epithelial (RPE) disturbance—including pigment clumping and/or dropout, RPE detachment, geographic atrophy, subretinal neovascularization and disciform scar. Not all these manifestations are needed for AMD to be considered present. The prevalence of persons with ophthalmoscopically or photographically identifiable drusen increases with age, and most definitions of AMD include drusen as a requisite. However, drusen alone do not seem to be directly associated with vision loss. It is rather, the association of drusen with the vision-threatening lesions of AMD, i.e., geographic atrophy, RPE detachment and subretinal neovascularization, that has led to their inclusion in the definition of AMD. Although recent studies have demonstrated the benefit of laser photocoagulation in those individuals with macular degeneration who develop acute, extrafoveal choroidal neovascularization, no treatment has been shown to be of benefit to the majority of people who have AMD. The cause of macular degeneration is unknown.

Recently, attention has been focused on the possible involvement of various minerals in retinal disease. Zinc has received particular notice in this regard due to the observation of high concentrations of zinc in ocular tissues, particularly the retina, pigment epithelium and choroid. Zinc is an important micronutrient that plays an essential role in human growth and function. Zinc is necessary for the activity of over a hundred enzymes, including carbonic anhydrase, superoxide dismutase and alkaline phosphatase. Zinc acts as a cofactor for numerous metalloenzymes, including retinol dehydrogenase and catalase. Zinc also is a cofactor in the synthesis of extracellular matrix molecules, is essential for cell membrane stability, is needed for normal immune function, is associated with melanin and is taken up in a facilitated manner by the retinal pigment epithelium. Despite the evidence supporting the notion that zinc must be essential to the metabolism of the retinochoroidal complex, relatively little is known of its role in the maintenance of normal eye function.

Toxicity from free radicals and oxidizers has also generated significant interest with regard to macular degeneration and the progression thereof. Circumstantial evidence indicates that protection against phototoxicity and oxidizers, such as would be provided by antioxidants, could slow the onset and progression of age-related macular degeneration as well as cataracts. If a treatment modality could slow down the progression of macular degeneration and/or cataracts, it would have a tremendous impact on the number of individuals who suffer from such problems due to the fact that such problems generally occur at significantly more advanced ages.

Accordingly, a need still exists in the art to provide methods and compositions for the treatment of macular degeneration and/or cataracts in the absence of surgery.

SUMMARY OF THE INVENTION

The present invention is a nutritional or dietary supplement composition for administration to humans or other animals that strengthens and promotes retinal health through the prevention, stabilization, reversal and/or treatment of visual acuity loss in people with particular ocular diseases. The present nutritional or dietary supplement composition may also be administered to prevent, stabilize, reverse and/or treat cataract development. The present nutritional or dietary supplement composition preferably comprises an effective amount of specific antioxidants and high-dosage zinc to decrease visual acuity loss. Visual acuity loss is decreased through the use of the present composition by reducing the risk of developing late stage or advanced age-related macular degeneration in persons with early age-related macular degeneration. The present composition may likewise reduce the risk of visual acuity loss associated with the development of cataracts.

The present invention likewise provides a method of treating a human or other animal by administering a nutritional or dietary supplement composition comprising an effective amount of specific antioxidants and high-dosage zinc to decrease visual acuity loss. The practice of this invention involves supplementing the diet of humans or animals by oral, intraperitoneal, intravenous, subcutaneous, transcutaneous or intramuscular routes of administration with the subject antioxidant and high-dosage zinc formulation.

The present invention likewise provides a method of manufacturing a nutritional or dietary supplement composition comprising an effective amount of specific antioxidants and high-dosage zinc to decrease visual acuity loss.

Accordingly, it is an object of the present invention to provide a nutritional or dietary supplement composition effective in the prevention, stabilization, reversal and/or treatment of macular degeneration and/or visual acuity loss.

Another object of the present invention is to provide a safe nutritional or dietary supplement composition for the prevention, stabilization, reversal and/or treatment of macular degeneration and/or visual acuity loss.

Another object of the present invention is to provide an effective method of preventing, stabilizing, reversing and/or treating macular degeneration and/or visual acuity loss.

Another object of the present invention is to provide a safe method of preventing, stabilizing, reversing and/or treating macular degeneration and/or visual acuity loss.

Another object of the present invention is to provide a method of manufacturing a safe nutritional or dietary supplement composition for the prevention, stabilization, reversal and/or treatment of macular degeneration and/or visual acuity loss.

Still another object of the present invention is to provide a method of manufacturing a nutritional or dietary supplement composition effective in the prevention, stabilization, reversal and/or treatment of macular degeneration and/or visual acuity loss.

These and other objectives and advantages of the present invention, some of which are specifically described and others that are not, will become apparent from the detailed description and claims that follow.

DETAILED DESCRIPTION

The following detailed description is provided to enable any person skilled in the art to which the present invention pertains to make and use the same, and sets forth the best mode contemplated by the inventors of carrying out the subject invention.

The preferred nutritional or dietary supplement composition of the present invention is a formulation of five essential ingredients preferably in quantities not less than those set forth below in Table 1, to be ingested daily.

TABLE 1

| Composition | Daily Dosage |
| --- | --- |
| Ascorbic acid | 450 milligrams (mg) |
| dl-alpha tocopheryl acetate | 400 international units (IU) |
| beta-carotene | 17.2 mg |
| zinc oxide | 68 mg |
| cupric oxide | 1.6 mg |

The subject composition is formulated to provide the above-listed essential ingredients at preferably not less than the daily dosage amounts specified above. This particular formulation of the subject composition has unexpectedly been shown in a multicenter prospective study of 4,757 persons, sponsored by the National Eye Institute of the National Institutes of Health, to provide a greater protective effect on the health of eyes than that achieved through the administration of a placebo, the antioxidant ingredients or the zinc/copper ingredients independently. The subject composition is preferably provided for oral administration in the form of lacquered tablets, unlacquered tablets, caplets or capsules. For purposes of simplicity only, throughout the remainder of this detailed description lacquered tablets, unlacquered tablets, caplets and capsules will each be referred to as simply "tablets" without distinction in form or function therebetween.

The preferred daily dosage of the subject composition as specified above may be administered in the form of two or more tablets. Most preferably the daily dosage of the subject composition is provided in the form of one tablet taken twice daily, for a total of two tablets a day, or in the form of two tablets taken twice daily, for a total of four tablets a day. Compared to taking the total daily dose once a day, twice daily dosing of half the total daily dose in one or more tablets per dose provides improved absorption and better maintenance of blood levels of the essential ingredients. Accordingly, if two tablets of the preferred formulation of the subject composition are to be ingested each day, each tablet is formulated to preferably provide not less than approximately 225 mg ascorbic acid, approximately 200 IU dl-alpha tocopheryl acetate, approximately 8.6 mg beta-carotene, approximately 34 mg zinc oxide and approximately 0.8 mg cupric oxide upon oral administration. If four tablets of the preferred formulation of the subject composition are to be ingested each day, each tablet is formulated to preferably provide not less than approximately 112.5 mg ascorbic acid, approximately 100 IU dl-alpha tocopheryl acetate, approximately 4.3 mg beta-carotene, approximately 17 mg zinc oxide and approximately 0.4 mg cupric oxide upon oral administration.

Tablets of the preferred formulation of the subject composition contain larger quantities of essential ingredients per tablet than the minimum quantities per tablet specified above. The minimum quantities specified above, per tablet, reflect the minimum amount of each essential ingredient to be provided upon oral administration through to the date of tablet expiration as set forth on the tablet sale label. However, since essential ingredients are subject to degradation over time, the tablets must contain larger quantities of essential ingredients to compensate for ingredient degradation. By providing larger quantities of essential ingredients in each tablet, one is ensured that even with ingredient degradation, one hundred percent of the ingredient amount specified on the tablet sale label is provided upon oral administration of the tablet through to the specified expiration date of the tablet. Another consideration in formulating the subject composition is that depending on the source of the individual ingredients, individual ingredient degradation rates may vary. For example, depending on the source of beta-carotene, a quantity of approximately 10 percent to a quantity of approximately 60 percent more beta-carotene may be necessary per tablet to provide the specified amount of beta-carotene per tablet as that listed on the tablet sale label through to the expiration date of the product. Accordingly, the specific formulation of the subject composition will vary depending on the sources of the individual ingredients and the specified length of product shelf life before expiration. Typically, the product shelf life for nutritional or dietary supplements is approximately two to three years. Such ingredient overages to compensate for ingredient degradation is reflected in the preferred ingredient percentage weight per tablet information provided below. Tablet formulations may also vary somewhat depending on slight deviations from manufacturing specifications within controlled tolerance ranges as customary within the field of art.

Variations contemplated in administering the subject composition to humans or other animals include, but are not limited to, providing time-release tablets or tablets manufactured to be administered as a single dose or as other multiple part dosages. Additionally, alternative avenues of administration besides oral administration are contemplated herein such as for example, but not limited to, intraperitoneal, intravenous, subcutaneous, sublingual, transcutaneous, intramuscular or like forms of administration. Each tablet of the subject composition preferably contains the following essential ingredients in the quantities specified below including overages to compensate for ingredient degradation. For purposes of simplicity only, formulations of the subject composition are provided below in accordance with a four-tablet oral daily dosage regime as described above.

Vitamin C

Vitamin C is a well known water-soluble antioxidant. Humans depend on external sources of vitamin C to meet their vitamin C requirements. Vitamin C in the form of ascorbate is found in the aqueous humor of human eyes. A high concentration of ascorbate in the aqueous humor of eyes is maintained by active transport of ascorbate from the blood stream to the posterior chamber of the eyes. Maximum aqueous humor ascorbate concentration occurs with a blood plasma ascorbate level in the range of approximately 0.3 to 0.5 milligrams/deciliter (mg/dl).

The U.S. recommended dietary allowance (RDA) for vitamin C in the form of ascorbic acid is 60 mg. Very large daily doses of vitamin C have been taken over many years with no or only minor undesirable effects. Intakes of 1,000 mg or more of vitamin C can be consumed daily without any known adverse effects. The subject composition provides a daily dose of not less than preferably approximately 450 mg of vitamin C. Accordingly, preferably each tablet of a four tablet per day dosage regime of the subject composition delivers not less than approximately 112.5 mg of vitamin C, but more preferably approximately 125 mg vitamin C, in the form of ascorbic acid. Such a formulation provides a total daily dosage of preferably not less than approximately 450 mg, but more preferably approximately 500 mg, and preferably not more than approximately 600 mg of vitamin C. This daily dosage of vitamin C is equivalent to approximately 7 to 10 times the RDA. In order to provide approximately 112.5 mg of vitamin C per tablet, approximately 5 to 50 percent, but more preferably 5 to 25 percent, but most preferably approximately 10 to 12 or 10.5 percent by weight of each tablet, including active as well as inactive ingredients, is ascorbic acid. This weight percentage for vitamin C may represent up to an approximately twenty percent overage per tablet or approximately 22.5 mg of additional ascorbic acid per tablet to compensate for natural degradation of ascorbic acid over the shelf life of the tablet.

Ascorbic acid is the preferred source of vitamin C in the subject tablets, although other sources such as for example sodium ascorbate could alternatively be used.

Vitamin E

Vitamin E is also a well-known antioxidant. Vitamin E can work synergistically with vitamin C in protecting vital cell function from normal oxidants. Vitamin E is a relatively non-toxic fat-soluble vitamin. Vitamin E is readily oxidized thereby significantly reducing its activity during periods of storage prior to ingestion. Once ingested, vitamin E is stored within the body and can contribute to the total body pool of vitamin E for up to one year.

The RDA of vitamin E in the form of dl-alpha tocopheryl acetate is 30 IU. No adverse effects of dl-alpha tocopheryl acetate have been observed at levels as high as 800 mg, with 1.0 mg of dl-alpha tocopheryl acetate being equal to 1 IU of dl-alpha tocopheryl acetate. Preferably each tablet of a four tablet per day dosage regime of the subject composition provides not less than approximately 100 IU of vitamin E in the form of dl-alpha tocopheryl acetate. Such a formulation provides a total daily dosage of preferably not less than approximately 400 IU, and preferably not more than approximately 540 IU, of vitamin E. This daily dosage of vitamin E is equivalent to approximately 13 to 18 times the RDA for vitamin E. Accordingly, vitamin E represents approximately 5 to 45 percent, but more preferably approximately 5 to 35 percent, but most preferably approximately 8 to 11 or 9.7 percent by weight of each tablet including active as well as inactive ingredients as described in greater detail below. This weight percentage for dl-alpha tocopheryl acetate may represent up to an approximately thirty percent overage per tablet or approximately 30 IU of additional dl-alpha tocopheryl acetate per tablet to compensate for the natural degradation thereof over the shelf life of the tablet.

Dl-alpha tocopheryl acetate is the preferred source of vitamin E in the subject tablets although other sources of vitamin E, such as for example trimethyl tocopheryl acetate and/or vitamin E succinate, may be used in the alternative.

Beta-Carotene

Beta-carotene, a proform of vitamin A, is a lipid-soluble orange pigment found in many vegetables. Beta-carotene is converted to vitamin A in the body with an efficiency of approximately 50 percent. The RDA of vitamin A is 5,000 IU. Beta-carotene has one of the highest antioxidant potentials of the antioxidants. No observed adverse effects are observed for beta-carotene at dosage levels as high as 25 mg per day for healthy, non-smokers. However, an increased risk of fatal coronary heart attacks in men with previous myocardial infarction and an increased risk of lung cancer among male smokers has been observed in individuals who receive 20 mg/day of beta-carotene. Preferably each tablet of a four tablet per day dosage regime of the subject composition provides not less than approximately 4.3 mg, but more preferably approximately 6 mg, of beta-carotene. Such a formulation provides a total daily dosage of preferably not less than approximately 17.2 mg, but more preferably approximately 24 mg, of beta-carotene and preferably not more than approximately 28 mg beta-carotene. At a potency of 1,667 IU vitamin A per mg beta-carotene, this daily dosage of beta-carotene is equivalent to approximately 6 to 10 times the RDA of vitamin A. Approximately 4.3 mg of beta-carotene represents approximately 0.2 to 4 percent, but more preferably approximately 0.2 to 3 percent, but most preferably approximately 0.51 percent by weight of each tablet including active as well as inactive ingredients as described in more detail below. This weight percentage for beta-carotene may represent approximately a thirty to seventy percent overage per tablet or approximately 1 to 2.5 mg of additional beta-carotene per tablet to compensate for natural degradation thereof over the shelf life of the tablet.

Beta-carotene is preferred in the subject composition due to its ready commercial availability although alternative carotenoid proforms of vitamin A could likewise be used.

Zinc

Zinc is important in maintaining the health of an eye's retina and is an essential part of more than 100 enzymes involved in digestion, metabolism, reproduction and wound healing. The RDA for zinc is approximately 15 mg. In one study, 80 mg of zinc was shown to be significantly better than placebo in retarding macular degeneration changes. (Newsome, Arch Ophthalmol 106: 192-8, 1988.) About 200 mg dosage of zinc per day, although well tolerated, has been shown to have potential side effects such as anemia. The anemia associated with high dosage zinc intake is attributable to copper deficiency. Diet supplementation with copper does not appear to have a deleterious effect on zinc absorption. Accordingly, preferably each tablet of a four tablet per day dosage regime of the subject composition provides not less than approximately 17 mg, but more preferably 20 mg, of zinc. Such a formulation provides a total daily dosage of not less than approximately 68 mg, but more preferably 80 mg, of zinc and preferably not more than approximately 100 mg of zinc. This daily dosage of zinc is equivalent to approximately 4 to 7 times the RDA for zinc. Accordingly, zinc represents approximately 0.8 to 8 percent, but more preferably approximately 0.8 to 4 percent, but most preferably 1.69 percent by weight of each tablet including active as well as inactive ingredients as described in more detail below. This weight percentage for zinc may represent an approximately fifteen to thirty-five percent overage per tablet or approximately 3 to 6 mg of additional zinc per tablet to assure potency of the product over the shelf life of the tablet.

Zinc is preferred in the form of zinc oxide in subject tablets due to the fact zinc oxide provides the most concentrated form for elemental zinc and is well tolerated in the digestive system. However, other forms of zinc such as for example zinc gluconate may alternatively be used or be used in combination with zinc oxide in the subject composition.

Copper

Copper, like zinc, is another important cofactor for metalloenzymes, and is a second necessary cofactor for superoxide dismutase. Two mg is the RDA for copper. Accordingly, preferably each tablet of a four tablet daily dosage regime contains not less than approximately 0.4 mg, but more preferably approximately 0.5 mg, of copper. Such a formulation provides a total daily dosage of not less than approximately 1.6 mg, but more preferably approximately 2 mg, of copper and preferably not more than approximately 2.4 mg copper to eliminate or minimize any potential undesirable effects of high dosage zinc. Accordingly, copper represents approximately 0.02 to 0.2 percent, but preferably approximately 0.02 to 0.1 percent but most preferably approximately 0.04 percent by weight of each tablet including active as well as inactive ingredients as described in more detail below. This weight percentage for copper represents approximately a twenty-five to sixty percent overage per tablet or approximately 0.10 to 0.25 mg of additional copper per tablet to ensure product potency over the shelf life of the tablet.

Copper in the form of cupric oxide is preferred in the subject tablets to help prevent zinc induced copper deficiency anemia, although other forms of copper such as for example copper gluconate may alternatively be used or used in combination with cupric oxide in the subject composition.

Other ingredients believed to be of benefit in maintaining eye health may likewise be added to the nutritional or dietary composition of the present invention if desired. Such ingredients include for example but are not limited to lutein, zeaxanthine, alpha-lipoic acid, phenolic compounds such as for example but not limited to oligomeric proanthocyanidins, anthocyanosides and combinations thereof as is discussed in more detail below.

Lutein

Lutein, like beta-carotene, is a carotenoid. Lutein is one of the most abundant carotenoids found in fruits and vegetables. Lutein is also an antioxidant found in the retina of healthy eyes. Preferably each tablet of a four tablet per day dosage regime could provide approximately 0.25 to 10 mg of lutein for a total daily dosage of approximately 1 to 40 mg depending upon whether lutein is used to supplement or substitute beta-carotene and/or zeaxanthine. As with beta-carotene, lutein is subject to degradation during periods of storage prior to ingestion. Accordingly, larger quantities of lutein are necessary in a tablet than the desired daily dosage quantity of lutein to be provided upon ingestion.

Zeaxanthine

Zeaxanthine, like lutein and beta-carotene, is a carotenoid. Zeaxanthine is found naturally in fruits and vegetables. Zeaxanthine is also an antioxidant found in the retina of healthy eyes. Preferably each tablet of a four tablet per day dosage regime could provide approximately 0.01 to 10 mg of zeaxanthine for a total daily dosage of approximately 0.04 to 40 mg depending upon whether zeaxanthine is used to supplement or substitute beta-carotene and/or lutein. As with beta-carotene, zeaxanthine is subject to degradation during periods of storage prior to ingestion. Accordingly, larger quantities of zeaxanthine are necessary in a tablet than the desired daily dosage quantity of zeaxanthine to be provided upon ingestion.

Lutein-Zeaxanthine

Lutein-zeaxanthine raw material combinations achieved deliberately, because of normal composition, or through raw material contamination may likewise be added to the subject composition as desired. Preferred ratios of lutein-zeaxanthine for example include 90 to 99 percent lutein and 1 to 10 percent zeaxanthine or 90 to 99 percent zeaxanthine and 1 to 10 percent lutein. Preferably each tablet of a four tablet per day dosage regime could provide approximately 0.01 to 10 mg of lutein-zeaxanthine for a total daily dosage of approximately 0.04 to 40 mg depending upon whether lutein-zeaxanthine is used to supplement or substitute beta-carotene.

Alpha-Lipoic Acid

Alpha-lipoic acid provides superior antioxidant protection due to the fact that it enhances the potency of other antioxidants in the body. Alpha-lipoic acid may be added to the nutritional or dietary supplement composition of the present invention if desired. If so desired, preferably each tablet of a four tablet per day dosage regime would provide approximately 0.25 to 5 mg of alpha-lipoic acid for a total daily dosage of approximately 1 to 20 mg.

Phenolic Compounds

Phenolic compounds such as for example but not limited to oligomeric proanthocyanidins are additional useful antioxidants. Oligomeric proanthocyanidins are found naturally in grape seeds. Phenolic compounds may be added to the nutritional or dietary supplement composition of the present invention if desired. If so desired, preferably each tablet of a four tablet per day dosage regime would provide approximately 0.25 to 5 mg of phenolic compounds for a total daily dosage of approximately 1 to 20 mg.

Anthocyanosides

Anthocyanosides are useful antioxidants found naturally in bilberry fruit. Anthocyanosides may be added to the nutritional or dietary supplement composition of the present invention if desired. If so desired, preferably each tablet of a four tablet per day dosage regime would provide approximately 0.25 to 5 mg of anthocyanosides for a total daily dosage of approximately 1 to 20 mg.

As noted above, inactive ingredients well known in the art are preferably present in the subject tablets to aid in manufacturing the subject composition in tablet form. For example, inactive ingredients may include but are not limited to binders, lubricants and disintigrants such as for example cellulose, gelatin, magnesium stearate, water, vegetable oil, glycerin, beeswax and silica.

The unique formulation of essential ingredients of the nutritional or dietary supplement composition of the present invention was demonstrated in a National Eye Institute (NIH/ADAMHA), multicenter, cohort study of 4,757 participants, to provide benefit for safe and effective prevention, stabilization, reversal and/or treatment of macular degeneration or visual acuity loss. The essential ingredients of the subject nutritional or dietary supplement composition, considered individually, have been known to provide certain physiological effects. However, the subject unique formulation and the effects thereof on eye health were not previously known.

A safe and effective method of preventing, stabilizing, reversing and/or treating macular degeneration or visual acuity loss by reducing the risk of developing late stage or advanced age-related macular degeneration in persons with early age-related macular degeneration and/or by reducing the risk of vision loss associated with the development of cataracts in accordance with the present invention consists of providing a human or other animal a daily dosage of not less than approximately 450 mg vitamin C, approximately 400 IU vitamin E, approximately 17.2 mg beta-carotene, approximately 68 mg zinc and approximately 1.6 mg copper. Preferably the daily dosage is provided in the form of two tablets taken twice daily or alternatively in the form of one tablet taken twice daily.

A method of manufacturing the nutritional or dietary supplement composition of the present invention, which is safe and effective in the prevention, stabilization, reversal and/or treatment of macular degeneration or visual acuity loss by reducing the risk of developing late stage or advanced age-related macular degeneration in persons with early age-related macular degeneration and/or by reducing the risk of vision loss associated with the development of cataracts, includes providing the essential ingredients in accordance with the formulation noted above. The essential ingredients of the subject composition, as well as any desired inactive ingredients and/or additive ingredients are combined by weight as described above and mechanically combined, such as for example, through the use of a blender to form a blend. If necessary, the blend is then tumbled until uniform. The blend is then compressed using a tablet press to form tablets. Optionally a coating may be sprayed on the tablets and the tablets tumbled until dry. Alternatively, the blend may be placed in mineral oil to form a slurry for containment in a soft gel capsule, the blend may be placed in a gelatin capsule or the blend may be placed in other dosage forms known to those skilled in the art.

While there is described herein certain specific embodiments of the present invention, it will be manifest to those skilled in the art that various modifications may be made without departing from the spirit and scope of the underlying inventive concept and that the same is not limited to the particular forms herein described except insofar as indicated by the scope of the appended claims.

We claim:

1. A method for stabilizing visual acuity loss in persons with early age-related macular degeneration comprising:
administering a daily dosage of not less than approximately 420 mg and not more than approximately 600 mg vitamin C, not less than approximately 400 IU and not more than approximately 540 IU vitamin E, approximately 0.04 mg to 40 mg lutein-zeaxanthine combination, not less than approximately 60 mg and not more than approximately 100 mg zinc and at least 1.6 mg and not more than approximately 2.4 mg copper.

2. The method of claim 1 wherein the administration of the dosage provides not less than approximately 68 mg zinc until an expiration date of said dosage.

3. The method of claim 1 wherein said vitamin C is provided in the form of ascorbic acid, and said vitamin E is provided in the form of dl-alpha tocopheryl acetate.

4. The method of claim 1 wherein said composition is supplemented with alpha-lipoic acid, phenolic compounds, anthocyanosides or a combination thereof.

5. The method of claim 1 wherein said zinc is provided in the form of zinc oxide, zinc gluconate or a combination thereof, and said copper is provided in the form of copper oxide, copper gluconate or a combination thereof.

6. The method of claim 1 wherein said daily dosage is administered orally in the form of one or more tablets taken daily.

7. The method of claim 1 wherein said daily dosage is administered orally in the form of two tablets taken twice daily.

8. A method of treating age-related macular degeneration consisting essentially of administering a daily dosage of not less than approximately 420 mg and not more than approximately 600 mg vitamin C, not less than approximately 400 IU and not more than approximately 540 IU vitamin E, approximately 0.04 mg to 40 mg lutein-zeaxanthine combination, not less than approximately 60 mg and not more than approximately 100 mg zinc and at least 1.6 mg and not more than approximately 2.4 mg copper, wherein the daily dosage stabilizes visual acuity loss by reducing the risk of developing late stage or advanced age-related macular degeneration in persons with early age-related macular degeneration.

9. The method of claim 8 wherein the administration of the daily dosage provides not less than approximately 68 mg zinc until an expiration date of the daily dosage.

10. The method of claim 8 wherein the daily dosage is administered orally in the form of two tablets taken twice daily.

11. A method for treating visual acuity loss in persons with early age-related macular degeneration, the method comprising administering a daily dosage composition comprising:
approximately 7 to 10 times the RDA of vitamin C;
approximately 13 to 18 times the RDA of vitamin E,
approximately 6 to 10 times the RDA of vitamin A in the form of beta-carotene, substituted or supplemented with lutein, zeaxanthine or a raw material combination thereof;
approximately 4 to 7 times the RDA of zinc;
and at least 1.6 mg and not more than approximately 2.4 mg copper.

12. The method of claim 11 wherein the administration of the dosage provides not less than approximately 68 mg zinc until an expiration date of said dosage.

13. The method of claim 11 wherein said vitamin C is provided in the form of ascorbic acid, and said vitamin E is provided in the form of dl-alpha tocopheryl acetate.

14. The method of claim 11 wherein the daily dosage composition is administered orally in the form of two tablets taken twice daily.

15. The method of claim 11 wherein said zinc is provided in the form of zinc oxide, zinc gluconate or a combination thereof, and said copper is provided in the form of copper oxide, copper gluconate or a combination thereof.

16. A method for treating visual acuity loss in persons with early age-related macular degeneration, the method comprising administering a daily dosage composition comprising:

approximately 7 to 10 times the RDA of vitamin C;
approximately 13 to 18 times the RDA of vitamin E,
approximately 1 mg to 40 mg of lutein,
approximately 0.04 mg to 40 mg zeaxanthine
approximately 4 to 7 times the RDA of zinc;
and not less than 1.6 mg and not more than 2.4 mg copper.

17. The method of claim 16 wherein the administration of the dosage provides not less than approximately 68 mg zinc until an expiration date of said dosage.

18. The method of claim 16 wherein said vitamin C is provided in the form of ascorbic acid, and said vitamin E is provided in the form of dl-alpha tocopheryl acetate.

19. The method of claim 16 wherein the daily dosage composition is administered orally in the form of two tablets taken twice daily.

20. The method of claim 16 wherein said zinc is provided in the form of zinc oxide, zinc gluconate or a combination thereof, and said copper is provided in the form of copper oxide, copper gluconate or a combination thereof.

* * * * *